(12) United States Patent
Agrahari et al.

(10) Patent No.: US 10,779,780 B2
(45) Date of Patent: Sep. 22, 2020

(54) SMART HANDLE APPARATUS AND METHOD FOR OPERATING A SMART HANDLE APPARATUS

(71) Applicant: KONINKLIJKE PHILIPS N. V., Eindhoven (NL)

(72) Inventors: Shailesh Kumar Agrahari, Pune (IN); Ravindra Bhat, Eindhoven (NL); Mansukh Amarashi Sheliya, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/322,378

(22) PCT Filed: Aug. 3, 2017

(86) PCT No.: PCT/EP2017/069585
§ 371 (c)(1),
(2) Date: Jan. 31, 2019

(87) PCT Pub. No.: WO2018/024802
PCT Pub. Date: Feb. 8, 2018

(65) Prior Publication Data
US 2019/0175127 A1  Jun. 13, 2019

(30) Foreign Application Priority Data
Aug. 5, 2016  (EP) .................................... 16183000

(51) Int. Cl.
*A61B 6/00* (2006.01)

(52) U.S. Cl.
CPC .......... *A61B 6/4441* (2013.01); *A61B 6/4405* (2013.01); *A61B 6/4482* (2013.01); *A61B 6/467* (2013.01)

(58) Field of Classification Search
CPC ... A61B 6/4405; A61B 6/4441; A61B 6/4482; A61B 6/467
See application file for complete search history.

(56) References Cited

U.S. PATENT DOCUMENTS

| 4,163,929 A | * | 8/1979 | Janu | A61B 6/0457 318/628 |
| 4,697,661 A | * | 10/1987 | Pajerski | A61B 6/4405 180/19.3 |
| 5,585,608 A | | 12/1996 | Kraemer | |
| 2001/0024487 A1 | * | 9/2001 | Akutsu | A61B 6/4405 378/198 |
| 2005/0094770 A1 | | 5/2005 | Fadler | |

(Continued)

FOREIGN PATENT DOCUMENTS

| DE | 4408128 A1 | 9/1995 |
| JP | 10225450 A | 8/1998 |

(Continued)

OTHER PUBLICATIONS

Binder, Norbert et al "The Surgeon's Third Hand an Interactive Robotic C-Arm Fluoroscope", Mobile Robotics Towards New Applications, ISBN 3-86611-314-5, pp. 784, 2006.

*Primary Examiner* — Chih-Cheng Kao

(57) ABSTRACT

The present invention relates to a medical device (100) having smart handle apparatus allowing the operation of a medical device as intended by a user.

14 Claims, 6 Drawing Sheets

(56) References Cited

U.S. PATENT DOCUMENTS

| | | |
|---|---|---|
| 2005/0100134 A1 | 5/2005 | Bauer |
| 2008/0069309 A1 | 3/2008 | Dorre |
| 2012/0087480 A1* | 4/2012 | Yang .................... A61B 6/4405 378/197 |
| 2012/0106701 A1 | 5/2012 | Meek |
| 2014/0328456 A1* | 11/2014 | Lee ........................ A61B 6/547 378/28 |
| 2015/0223892 A1* | 8/2015 | Miller .................... A61B 50/18 345/174 |
| 2015/0245965 A1 | 9/2015 | Griesel |

FOREIGN PATENT DOCUMENTS

| | | |
|---|---|---|
| JP | 2003230554 A | 8/2003 |
| JP | 2009291531 A | 12/2009 |
| JP | 2014233369 A | 12/2014 |

* cited by examiner

SMART HANDLE APPARATUS AND METHOD FOR OPERATING A SMART HANDLE APPARATUS

CROSS-REFERENCE TO PRIOR APPLICATIONS

This application is the U.S. National Phase application under 35 U.S.C. § 371 of International Application No. PCT/EP2017/069585, filed on Aug. 3, 2017, which claims the benefit of European Patent Application No. 16183000.5, filed on Aug. 5, 2016. These applications are hereby incorporated by reference herein.

FIELD OF THE INVENTION

The present invention relates to the technical area of medical devices. In particular, the present invention relates to a mobile surgery system comprising a smart handle apparatus, to a smart handle apparatus, to a method for controlling a smart handle apparatus, to a program element and to a computer readable medium.

BACKGROUND OF THE INVENTION

A mobile surgery system and in particular a mobile surgery imaging system including a C-arm, is a device with an X-ray source and an X-ray detector mounted on a C-shaped carriage system and is commonly used for orthopaedic surgeries, pain management, urology, vascular clinical segments. The C-arm helps to bring the X-ray system mounted on the C-arm into a position to make X-ray images of the relevant region of interest (ROI). Typically, an operator or technician maneuvers the C-arm while the surgeon is performing the surgery. During an operation, the surgeons communicate the desired positions of the C-arm axis to the technician or operator who is operating the C-arm. Due to the sterile environment and manual lock and/or unlock of the C-arm axes, joints or shafts, sometimes it may not be possible by surgeons themselves to move the C-arm axis during the surgical procedure. Thus, unwanted X-ray radiation may be provided to the patient and/or staff until the surgeon gets the desired region of interest (ROI).

The document "The Surgeon's Third Hand an Interactive Robotic C-Arm Fluoroscope", by Norbert Binder, Christoph Bodensteiner, Lars Matthäus, Rainer Burgkart and Achim Schweikard, Mobile Robotics Towards New Applications, ISBN 3-86611-314-5, edited by Aleksander Lazinica, pp. 784, ARS/PV, Germany, December 2006 relates to experiments with the fully robotized C-arm for movements in the image plane, longbone images, data acquisition for 3D reconstruction and landmark based positioning.

SUMMARY OF THE INVENTION

There may be a need to provide an efficient control of a functional device.

The object of the present invention is solved by the subject-matter of the independent claims, wherein further embodiments are incorporated in the dependent claims.

According to an aspect of the invention a mobile surgery imaging system having a smart handle apparatus for controlling the mobile surgery system is provided.

According to an aspect of the present invention a mobile surgery imaging system including a C-arm and a smart handle apparatus is provided, wherein the smart handle apparatus is configured to control movements of the imaging system, for example of the C-arm or of a carriage.

In an embodiment, the smart handle apparatus comprising a handle bar for operating the smart handle apparatus, a force determining device and a button device. The force determining device is adapted to determine the direction of a force applied to the handle bar in components of a three dimensional space. The button device is adapted to set or select a movement profile in form of groups of movements wherein each movement of the group of movements is linkable to a corresponding direction component of the three dimensional space determined by the force determining device. The smart handle apparatus is adapted to provide a control signal for the mobile surgery system. This control signal may comprise information about the movement profile and the direction of the force applied to the handle bar in components of a three dimensional space.

In an example, if the C-arm of a mobile surgery system is provided and the C-arm comprises an X-ray scanner, the smart handle apparatus may be mounted on the X-ray source or on the X-ray detector. Setting a movement profile may comprises activating a group of possible movements and/or deactivating another group of movements.

Thus, a distinct link between a force direction component and a certain movement within each group may be generated, while a plurality of movements in different groups may be linked to one and the same direction component of the applied force. In other words, a group of movements may exclude ambiguous links of directions to certain movements.

For example, in a C-arm system with five possible system movements as stated in Table 1, two movement profiles may be defined; a first profile with a group of three system movements (wig-wag/horizontal/height) each corresponding to one of an x, y or z direction, and a second profile with two further movements (orbital/propeller) each also corresponding to one of an x, y or z direction.

According to an aspect of the present invention a smart handle apparatus for a mobile surgery system or for a medical device is provided comprising a handle bar for operating the smart handle apparatus, a force determining device and a button device. The button device is adapted to set a movement profile in form of groups of movements wherein each movement is linkable to a corresponding direction component of the three dimensional space determined by the force determining device. The smart handle apparatus is further adapted to provide a control signal for the mobile surgery system, the control signal comprising information about the set movement profile and the direction of the force applied to the handle bar in components of a three dimensional space.

In an example the method for controlling the smart handle apparatus comprises determining the direction of a force applied to a handle bar of the smart handle apparatus in components of a three-dimensional space. In other words, the smart handle apparatus is adapted to divide or separate an applied force in three components, which are in line with the three directions or axes of a Cartesian coordinate system.

According to yet another aspect of the invention a method for controlling a smart handle apparatus is provided. The method comprises determining the direction of a force applied to a handle bar of the smart handle apparatus in components of a three dimensional space. Furthermore, the method provides for setting a movement profile in form of groups of movements by a button device wherein each movement is linkable to a corresponding direction component of the three dimensional space determined by the force determining device. The method also comprises providing a control signal wherein the control signal comprises information about the movement profile and the direction of the force applied to the smart handle apparatus in components of a three dimensional space.

In an example the control signal may be used to control a medical surgery system. In a further example the method further comprises determining the strength of each component in each direction of the three-dimensional space. Further, by using the method, the orientation of the handle bar may be determined.

In other words the determined directions of the force applied to the handle bar, a switching signal received from a button device for switching between groups of movements which are operated by the same component of the three-dimensional space and/or the determined orientation of the handle bar are parameters which can be mapped to a predefined movement profile. As an output of executing the method, a control signal for a medical surgery system is generated, the signal may comprise at least one of a movement profile, a direction and a strength of the force in each direction.

In this way it may be possible to detect the intension of a user who operates the smart handle apparatus. In one example the control signal may comprise raw data from the relevant sensors of the smart handle apparatus. The sensors of the smart handle apparatus may comprise the force determining device, the button device, the orientation determining device and/or the safety switch. In another example the control signal may comprise processed information from the corresponding sensors. Processed information may be information that can be used to directly control the mobile surgery system. In an example the processed information may comprise control information for particular joints, brakes and/or wheels of the mobile surgery system. Processed may be output by the mapping device. The mapping device may be integrated into the smart handle apparatus and/or the mapping device may be arranged externally to the smart handle apparatus.

According to another aspect of the present invention, a program element for controlling a smart handle apparatus is provided, which, when being executed by a processor, is adapted to carry out the method for controlling a smart handle apparatus.

According to yet another aspect of the present invention, a computer-readable medium, such as a CD-ROM, comprising a program code is provided, which, when being executed by a processor, is adapted to carry out the method for controlling a smart handle.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

The smart handle may be provided at the C-arm of the mobile surgery system. By using the smart handle, the surgeon can take care of the C-arm positioning in an intuitive manner. The smart handle is designed to sense a user request for each axis of the mobile surgery system to unlock for free movement. For example, a brake for a shaft of a corresponding joint and/or a brake of a wheel is released in order to allow a movement about a corresponding axis. For triggering a rotational movement about axes, in an example the user may press a safety switch before applying the force. For translational axes additionally one of the provided control switches or buttons may be pressed along with the safety switch. The smart handle comprises force-sensitive resistor (FSR) sensors to sense the user request for each axis. Based on the FSR signal, it is determined whether the force for a certain direction exceeds a predetermined threshold; if so, the respective movement axis is unlocked.

According to an aspect of the invention the smart handle apparatus of the mobile surgery system further comprises an orientation determining device. The orientation determining device is adapted to determine the orientation of the handle bar. The smart handle apparatus is further adapted to provide information about the determined orientation of the handle bar in the control signal.

The handle apparatus can be operated in many directions e.g. in a longitudinal direction. Dependent on the orientation of the longitudinal axis of the smart handle the movement in the longitudinal direction may be mapped to a vertical or horizontal movement. An orientation determining device may help to make a correct translation of the installed orientation to the movement intention of the user and finally to the correct control signal.

In an example, the smart handle apparatus may be implemented as a joystick, as a mouse device, as a knob or as a lever.

According to another aspect of the present invention the force determining device of the smart handle apparatus is further adapted to determine the strength of each component of the force in each direction of the three dimensional space. The smart handle apparatus is further adapted to provide information about the determined strength of each component of the force in each direction of the three dimensional space in the control signal.

Determining the strength of force may allow for determining a velocity of a movement if for example joints are driven by motors and/or the strength may allow for controlling the strength of a brake for a corresponding axis.

According to another aspect of the present invention the smart handle apparatus of the mobile surgery system further comprises a mapping device. The mapping device is adapted to map the information of the control signal to a predefined movement of the set movement profile.

In an example, input signals to the mapping device are raw sensor signals, e.g. within a control signal. The control signal may also comprise information about the relevant group of possible movements. In this case the mapping device may be integrated in the mobile surgery system. In another example the mapping device may be integrated into the smart handle device. In such a case the smart handle apparatus may provide pre-processed control signals. The mapping device may be adapted to map raw signals to control signals that can directly be provided to actors of the medical surgery system. Such actors may be selected from the group of actors consisting of a motor operating a joint, a brake for locking or unlocking a joint, a motor of a wheel and/or a brake of a wheel.

The smart handle apparatus in combination with the button device allows for analyzing the intention of a user who is operating the C-arm of the mobile surgery system.

This intention can be represented by signals for corresponding actors generated by detected force directions and a selected movement profile.

According to an aspect of the present invention, the movement profile comprises a selection of a height positioning movement, a horizontal movement, a propeller movement, a wig-wag movement and an orbital movement.

The different movements of the movement profile may be provided by the degrees of freedom (DOF) of the different axes, shafts, axles and joints implemented in the medical surgery system. A movement profile may comprise a group of movements specific for that particular movement profile. The movements for the group of movements associated with a movement profile may be selected as a sub-group of the group of all possible movements. The group of all possible movements may consists of a height positioning movement, a horizontal movement, a propeller movement, a wig-wag movement and an orbital movement. In an example two different movement profiles are differentiated by comprising at least one movement that is ambiguous with regard to a force direction signal provided by a direction determining sensor. In an example a force directed into the longitudinal axis of the smart handle apparatus may ambiguously be mapped to a wig-wag movement or to a propeller movement. In order to determine a movement profile a building rule is considered that ensures that these ambiguous movements are associated with different movement profiles. In other words, the movement profiles are generated such that every movement of the movement profile unambiguously can be mapped to a direction component determined by the force determining device.

According to another aspect of the present invention, the smart handle apparatus further comprises a second button device for switching between the groups of movement. The second button device is adapted to set a movement profile in form of groups of movements wherein the second button device is arranged in a predefined distance from the button device.

The second button may allow for a person who is left-handed to comfortably operate the smart handle in the same way as a person who is right-handed and for whom the first button may be positioned. The functionality of the first and the second button device may be the same. The button can be used to indicate the intention of a user and to select a movement profile. Dependent on the switching state of the button device a group of possible movements is selected.

According to another aspect of the present invention, the smart handle apparatus is provided, wherein the force determining device comprises at least one of an optical sensor, a strain gauge sensor, a capacitive sensor and/or a potentiometer.

Using an optical sensor may allow for a precise force direction detection. Such a sensor can also be used for the strength detection into the relevant direction. Similar to an optical sensor, a sensitive resistor, a potentiometer or a capacitive sensor as well as a strain gauge sensor also allow for detecting the strength of the force as well as the direction of the force. By determining the strength of a force it may be possible to detect whether a threshold or force limit is exceeded. This information may be used to lock or unlock a brake for a joint. Determining the strength of a force may also allow for controlling a motor device by controlling a velocity proportional and/or motor torque proportional to the detected strength of the force.

According to another aspect of the present invention, the force determining device comprises a threshold, and the force determining device is adapted to prevent delivering of a signal below the threshold. Alternatively, the force determining device is adapted to only deliver a signal if the signal equals to or exceeds a predefined threshold.

Considering a threshold may also support a user operation in preventing an unintentional movement of the relevant component such as a C-arm of a functional device, if only a light force below a certain threshold is applied to the smart handle.

According to another aspect of the present invention, the smart handle apparatus comprises a safety switch, wherein the safety switch is adapted to prevent an unintentional operation.

The safety switch may be installed close to the smart handle apparatus in such a way, that if the smart handle is intended to be operated, the safety switch is triggered.

According to another aspect of the present invention, the orientation determining device is an accelerator sensor and/or a G-force sensor. Such a sensor may detect the orientation of the gravity field of the earth.

Using an orientation determining device it may be possible to determine a force into a reference direction, such as the direction of a gravity, and in this way to determine the orientation of the handle bar itself.

In an example, the method for operating the smart handle apparatus further comprises using the control signal for unlocking predetermined brakes of sub-devices of the mobile surgery system in order to enable predetermined manual motion of at least part of the mobile surgery system. A corresponding control signal for a braking device may be provided.

The smart handle apparatus may be adapted to determine which sub-device is to be operated by that force after detecting a force on the handle.

A smart handle apparatus or a smart handle allows to determine the orientation of the smart handle apparatus and by using this determination of an orientation to understand the intention of a movement desired by an operator of the handle. Since the mobile surgery system or the functional device such as an X-ray system with a C-arm is adapted to be movable into a plurality of different positions and orientations the intended movement by using the handle may be different dependent from the starting position and/or orientation of the sub-device, e.g. the C-arm or a corresponding joint or brake of a medical surgery system.

For example, if the handle is in a horizontal position, a longitudinal movement of the handle may be interpreted as a wig-wag movement desired for the C-arm. If, however, the smart handle is in a vertical position, the movement of the handle in the longitudinal direction may be the indication for a desired up and down movement. Thus, the orientation determining device may allow for differentiating movement allocation within a particular group of movements and/or within a particular movement profile dependent on the orientation and/or position of the smart handle apparatus.

Accordingly, the orientation of the handle bar can be taken into account in determining the control signal for the mobile imaging system in accordance with the user's intended movement. For example, when the handle bar is mounted on the C-arm itself, during rotation of the C-arm, the determined direction of the force on the handle bar may change with the rotation. This effect may be compensated for by the orientation determining device, for example resulting in an undisturbed and continuing rotation of the C-arm in accordance with the intent of the user.

In an example the force determining device may comprise a force direction determining device and/or a force strength determining device. In a particular example the force direction determining device and the force strength determining device are separate devices. In a further example the mapping device may be an external device and not part of the smart handle apparatus. In yet another example the mapping device may be connected to sensors of the smart handling apparatus via a serial communication interface. The mapping device may be realized as a processor running a computer program or as a hard wired device. The mapping device may be part of a controlling device. The force direction sensor may be adapted to determine the direction of a force applied to the handle bar in components of a three-dimensional space. The force strength determining device may be adapted to determine the strength of each component in each direction of the three-dimensional (3D) space.

The safety switch is automatically activated whenever a user grabs the handle, thus enabling rotational movements. When a control switch is operated, the C-arm rotational axes are locked and the translational axes are unlocked enabling, for example, movement of the carriage.

In one example, the smart handle is positioned on the image detector of the C-arm, and thus it may rotate with the arm. For this purpose, one or more accelerometers are provided to determine a current orientation of the smart handle and relate the different FSR signals to the 'correct' movement axes. This enables an intuitive control, independent of the current orientation. In an example the button device is adapted to switch between groups of movements which are operated by the same component or component of force of the three-dimensional space. The button device may be any device allowing for switching between at least two different states. Thus, forces directed into the same direction may result in different movements of the mobile surgery system or medical device dependent on the status of the button device or switching device. The orientation determining device is adapted to determine the orientation of the handle bar, and the mapping device is adapted to map the signals from the force direction determining device, the button device and/or the orientation determining device to a control signal dependent on the applicable movement profile. The smart handle apparatus is adapted to provide a control signal for the mobile surgery system, for the functional device or for the medical device, wherein the control signal may comprise information about the selected movement profile, the direction and/or the strength. In other words, the output signal from the smart handle apparatus may be a signal indicating the intention of a user operating the smart handle apparatus represented as a signal usable for other entities such as a mapping device and/or directly by an actor of the medical surgery system. The signal may be structured according to a transfer protocol and may also have coded bit patterns. The signal may be used to lock and/or unlock relevant joints or brakes of the medical surgery system. The control signal can be used for unlocking a lock of a certain axis and/or for controlling a motor of the corresponding axis in order to allow a force-controlled movement of the functional device in a particular direction.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
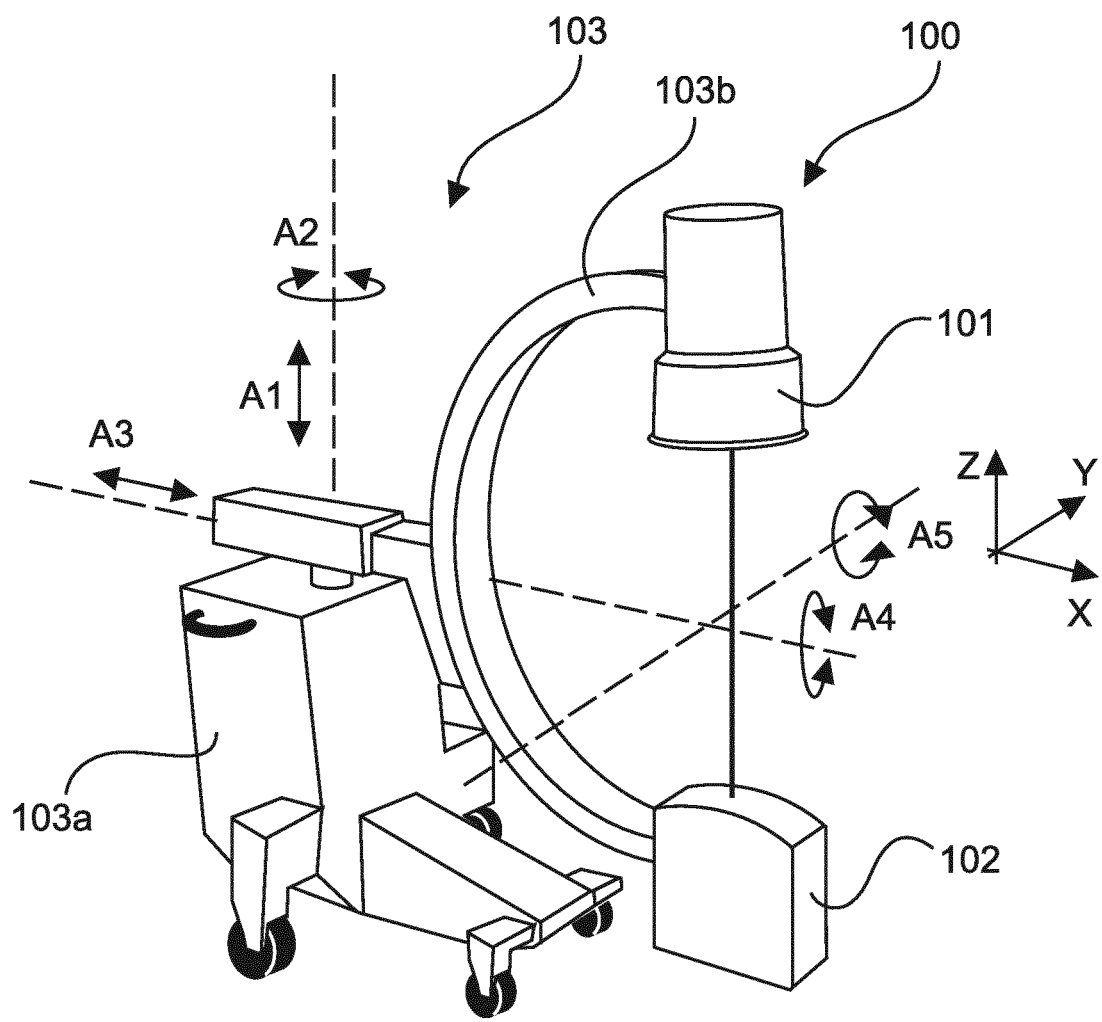
FIG. 1 shows a perspective view of a mobile surgery system with a C-arm according to an exemplary embodiment of the present invention.

FIG. 1 shows a perspective view of a mobile surgery system 100 with a C-arm according to an exemplary embodiment of the present invention. In particular FIG. 1 shows a mobile surgery imaging system including a C-arm provided with a smart handle apparatus according to an exemplary embodiment of the present invention. The mobile surgery system 100 comprises a carriage system 103 with movable parts 103a, 103b, detector parts 101, 102 and a processing part (not shown in FIG. 1). The C-arm 103b is a device having an X-ray source 101 and an X-ray detector 102 mounted on a C-shaped carriage system 103. The mobile surgery system 100 is commonly used for orthopaedic surgeries, pain management, urology, vascular clinical segments, etc. The carriage system 103 has a carrier 103a or a carriage 103a and a C-arm 103b. The mobile part 103 of the mobile surgery system 100 has five serial axes A1 to A5, which are linked to corresponding joints. The axis and the corresponding movement is provided in table 1.

TABLE 1

| Axis | Parameter | Movement | Name | Function |
| --- | --- | --- | --- | --- |
| A1 | d1 | Translational | Lift | Height Adjustment |
| A2 | Θ1 | Rotational | Wig-Wag | Rotation in x-y plane |
| A3 | d2 | Translational | Carriage | Arm-length adjustment |
| A4 | Θ2 | Rotational | Angulation | C-Rotation sideways |
| A5 | Θ3 | Rotational | Orbital | C-Rotation in C-plane |

In order to allow a movement around a certain axis a plurality of brakes may have to be released or unlocked. Axis A1 and a corresponding lift device is used for a lift movement and allows for a height adjustment. Axis A2 and the corresponding joint allows for a rotational movement which is used in a wig-wag movement and allows for a rotation in x-y-plane. A wig-wag movement may also be supported by wheels of the carriage 103a. Axis A3 and a corresponding arm device allow for a translational movement, a so-called carriage movement, and functions as arm-length adjustment. Axis A4 and a corresponding joint allow for a rotational movement which is also called angulation or propeller movement and functions as a C-rotation sideways. Axis A5 and a corresponding orbital device allow for another rotational movement of the C-arm in the C-plane, which is called an orbital movement.

The system provides real-time X-ray images of a patient undergoing a surgery by rotating the C-arm around the patient. An operator or technician maneuvers the C-arm while the surgeon is performing the surgery.

A joint arrangement in combination with the C-shape allows for positioning X-ray source 101 and X-ray detector 102 around the patient (not shown in FIG. 1). The patient is lying on the operating room table (OR-table). The lift movement which is along the A1-axis allows for a height adjustment. To support this type of movement the corresponding lift mechanism may be motor-driven. The motor may support a manual force. All other joints are moved by hand one after another. For moving the C-arm 103b manually, the brake of the relevant joint is released or unlocked so that the relevant joint can fulfil a free movement and a manual positioning is performed until the target position is reached. When the target position is reached, the corresponding joint is locked again (in FIG. 1 the joints are not shown). The axes A4 and A5 lie in different planes and do not intersect. Axis A5 is the C-plane axis and A4 is the propeller axis for a propeller movement. The steps involved in positioning the C-arm 103b with respect to patient at anatomical area of interest are made by a communication between the surgeon and the operator of the C-arm. The surgeon is instructing the technician in order to move the C-arm in a position the surgeon is needed. The mobile surgery system 100 or functional device 100 can use the axes A1 to A5 and corresponding joints, actors or devices in order to position the C-arm.

Figure 2:
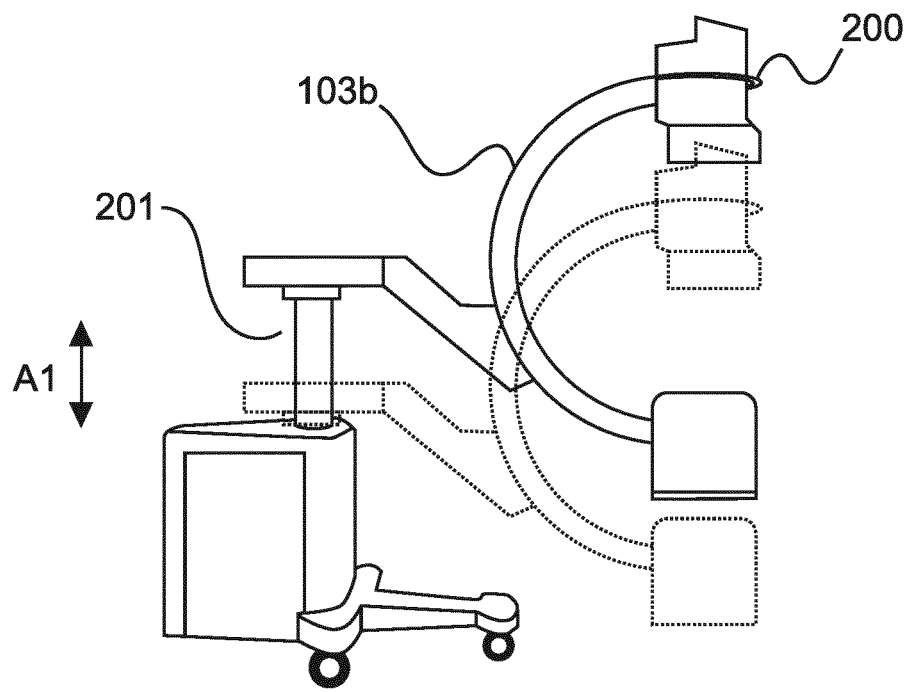
FIG. 2 shows a height positioning of a C-arm according to an exemplary embodiment of the present invention.

FIG. 2 shows a height positioning of a C-arm according to an exemplary embodiment of the present invention. For the height positioning, a translation along axis A1 is made using the lift 201.

Figure 3:
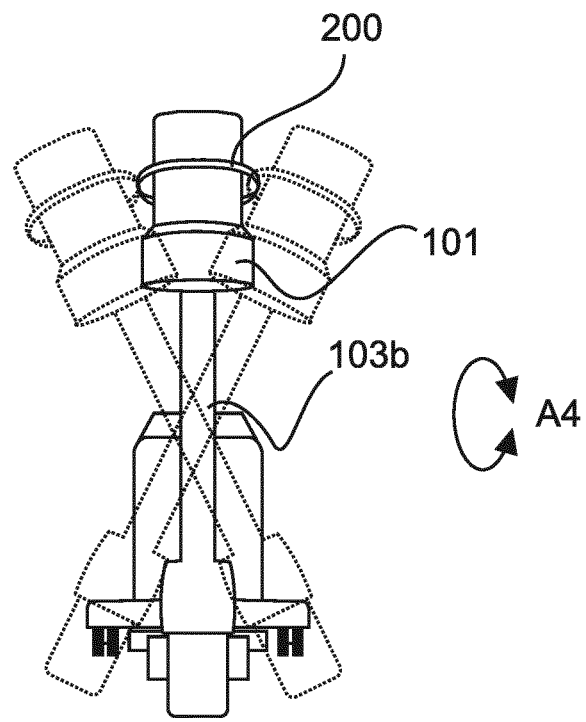
FIG. 3 shows a propeller movement of a C-arm according to an exemplary embodiment of the present invention.

FIG. 3 shows a propeller movement according to an exemplary embodiment of the present invention in order to turn the C-arm 103b around axis A4. A corresponding joint of the C-arm is released and the smart handle 200 can be used to move the X-ray source 101 into the desired position.

Figure 4:
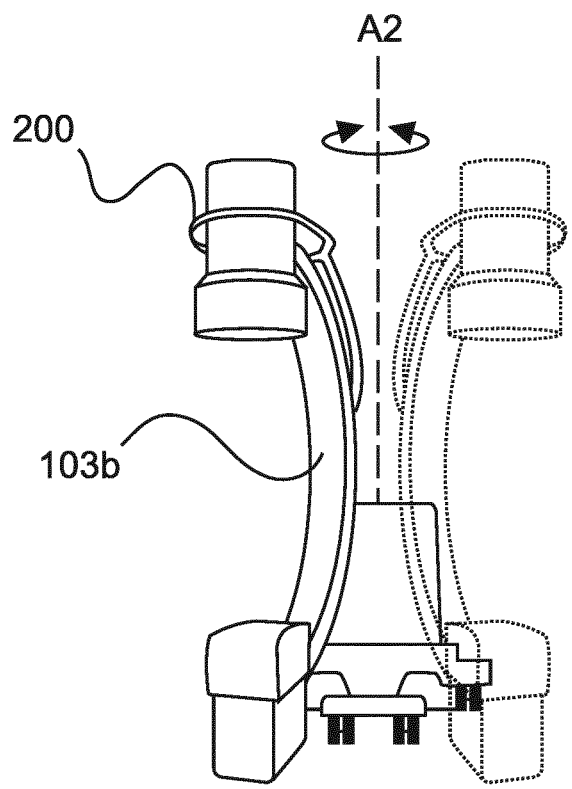
FIG. 4 shows a wig-wag movement of a C-arm according to an exemplary embodiment of the present invention.
Figure 5:
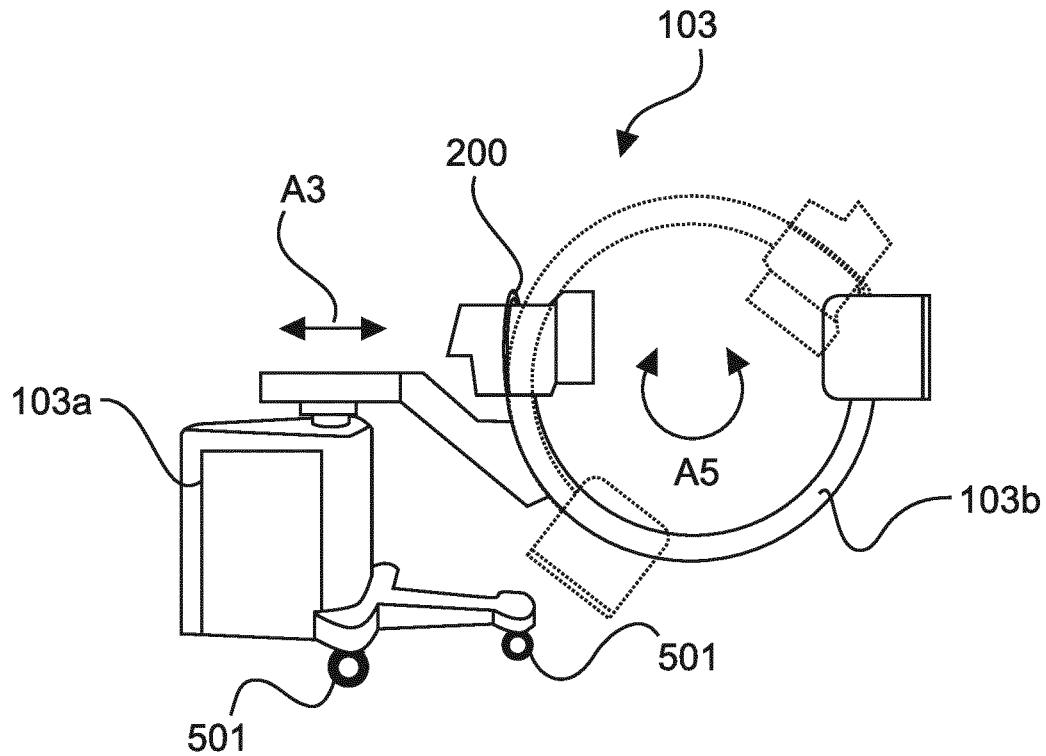
FIG. 5 shows a horizontal- and orbital movement of a C-arm according to an exemplary embodiment of the present invention.

FIG. 4 shows a wig-wag movement of C-arm 103b according to an exemplary embodiment of the present invention. Wig-wag movement is conducted by turning the C-arm 103b around axis A2 and releasing a corresponding joint in the carriage 103a. FIG. 5 shows a horizontal and orbital movement of a C-arm 103b according to an exemplary embodiment of the present invention. The horizontal movement is conducted by moving the C-arm along axis A3 relative to carriage 103a. Wheels 501 are used to move the mobile surgery system or the medical system 100 over the floor and may also support a wig-wag movement. In an example where carriage 103a has omni wheels installed a parallel movement may be executed by releasing brakes of wheels 501 and moving the whole system 103 parallel to the floor. If all wheels are omni wheels 501, i.e. wheels being able to move in any direction, and the wheels' direction is controlled by brakes, a movement where the front wheels are released in the direction of the right angle to the longitudinal axis and the back wheels are steered at the direction of the right angle to the longitudinal axis results in parallel motion of the system. An orbital movement is made by a rotation in the C-plane around axis A5.

As shown in FIG. 2 to FIG. 5, the mobile surgery system 100 has axes A1 to A5 that can be used to move the C-arm in order to position the human anatomy of interest within the field of view of the image chain. The term 'image chain' may be a term used to summarize the X-ray source 101, the detector 102, a frame grabber, a processing device and a display device of the image. The operator of the C-arm 103b needs to release a mechanical brake of respective movement, move towards the handle for releasing the brake, grab the respective handle and apply force to move the system. A smart handle may control the brakes or joints associated with a desired movement detected by the smart handle 200 and/or drive a motor to drive or assist the motion. The desired movements may be derived from determined force directions in combination with a selected movement profile.

Using the smart handle 200 may allow to obtain several images from the same viewing angle during the operation. By employing the handle, it is possible to find the same orientation again even after the joints were moved. For such a scenario more than one joint may be adjusted in general. For returning to a previous position it may be possible to employ a "store recall" mode. A "store recall" mode is an operation mode of the C-arm, where sensors and/or a processing device store(s) a position of the C-Arm, e.g. by storing the orientation and/or direction of the joints of the C-arm. When the C-arm is operated in the "store recall" mode the previously saved orientation of the C-arm or C-arc is used as reference. When the handle is used for moving the C-arm to the stored position sensors in the mobile surgery system measure the actual position of the C-arm and if the actual position equals to that of the reference, the system brakes lock in order to stop the motion.

By using a smart handle apparatus, the surgeon can move the C-arm in the desired position on its own without communicating the desired position of the C-arm axis to an operator. A manual locking and unlocking of the relevant joints is prevented and the inventive smart handle apparatus can also be used in a sterile environment. Therefore, it is possible by the surgeon to move the C-arm axis during the surgical procedures. The handle may have a detachable cover similar to the covers used in sterile operating light handles. In other words, the handle apparatus has mounting devices which allow for quickly mounting and unmounting the handle apparatus to/from the relevant mobile surgery system. This fact allows for removing the handle after use in order to sterilize the handle bar. After sterilization the handle bar may be returned inside a plastic bag that has to be removed before mounting the handle bar to the mobile surgery system again. If the surgeon moves the C-arm to the desired ROI (Region of Interest), the C-arm can precisely be positioned and unwanted X-ray radiation for patient and staff can be prevented that might be necessary until the surgeon gets the desired ROI. With the smart handle the surgeon can take control of the C-arm movement and take the X-ray images of the patient's anatomy.

As an example, with the described smart handle automated locking and unlocking of a mobile C-arm rotational and translational manual movement is possible in order to optimize the workflow and prevent mistakes during surgery procedure. By using the smart handle apparatus 200 it may be possible to save surgery procedure time and minimize X-ray radiation to patient and staff.

With the smart handle, automated manual locking and unlocking of mobile C-arm rotational and translational axis movements are possible. The smart handle apparatus can be used as a user interface to maneuver the C-arm at desired positions intuitively. Such intuitive positioning helps to reduce mistakes and may prevent mistakes during the surgery procedure. It can also help to minimize stress, surgery procedure time and radiation dose for a patient and staff.

Figure 6:
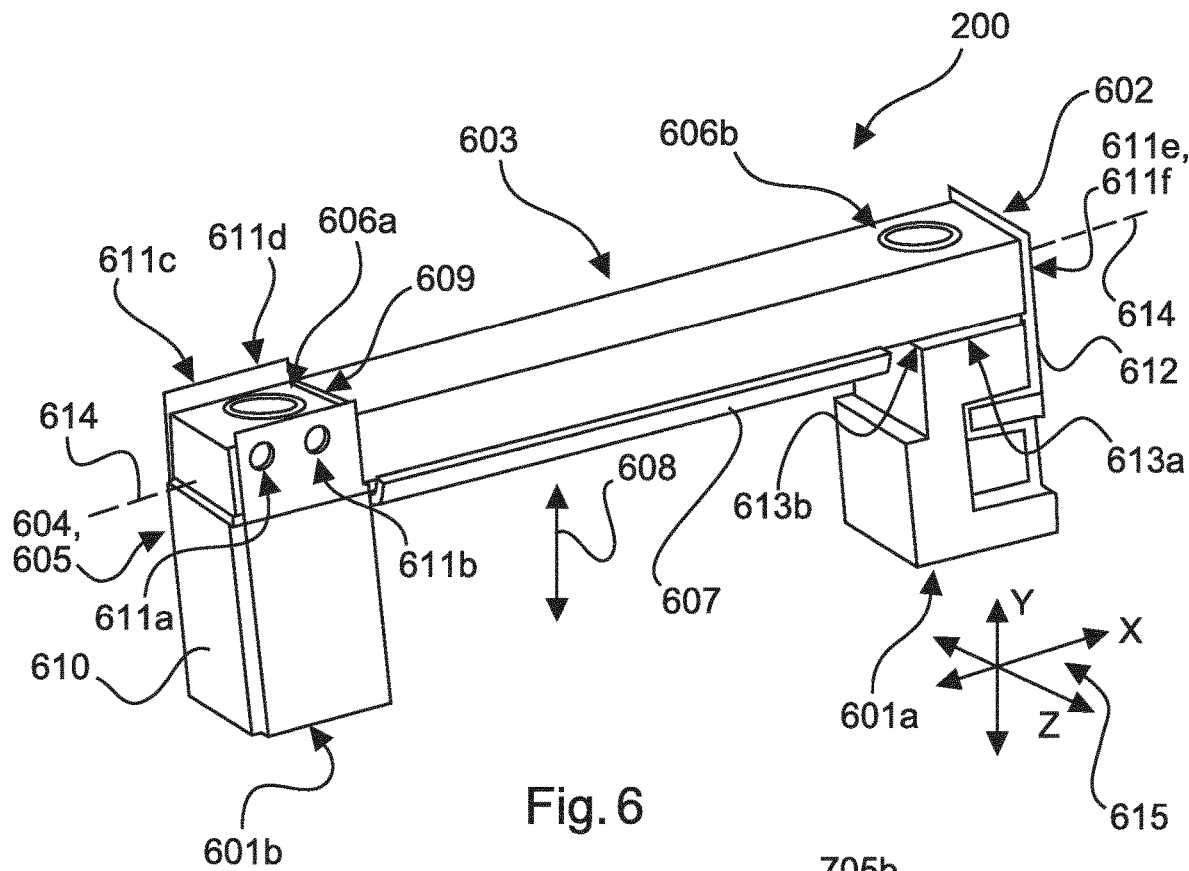
FIG. 6 shows a smart handle apparatus according to an exemplary embodiment of the present invention.

FIG. 6 shows the smart handle apparatus according to an exemplary embodiment of the present invention. The smart handle apparatus 200 can be used as user interface 200. This smart user interface 200 is designed to maneuver a mobile C-arm for rotational and translation axes with automated lock and unlock of each axis. By pressing or releasing the button 606a, 606b it is possible to differentiate between different movements, for example between translational and rotational movements, even if forces directed into the same directions may be applied to the handle for both movements. The smart user interface 200 or smart handle apparatus 200 provides sensing mechanism to detect the user request for each axis separately to unlock automatically the desired maneuver or movement profile. The smart handle apparatus 200 can be mounted to a mobile surgery system 100 or to a medical device 100 with the basis 601a, 601b.

The smart handle apparatus 200 may comprise an orientation determining device 602, 802a. The orientation determining device is adapted to determine a position and/or an orientation of the handle 200. In an example the orientation is determined as the deviation of the actual position from the direction of the gravity force. The orientation determining device 602, 802a may be a G-force sensor 602, 802a or an accelerator measurement device 602, 802a.

The smart handle 200 comprises a handle bar 603 for operating the smart handle apparatus. Furthermore, the smart handle apparatus has a force determining device 604, 605 which in FIG. 6 comprises a force strength determining devices 604 and force direction determining devices 605. The force strength determining device 604 and force direction determining device 605 are only partially shown in FIG. 6. The force strength determining devices 604, 605 may be realized as a single force determining device. Furthermore, the smart handle apparatus 200 has button devices 606a, 606b. Both button devices 606a, 606b have the same functionality and are implemented to make the operation comfortable for a left-handed person as well as for a right-handed person. Furthermore, the smart handle apparatus has a security switch device 607. The security switch device 607 is operated as indicated by arrow 608 when the handle bar 603 is grabbed.

Handle bar 603 has a weakening portion 609 which allows to slightly bend the handle bar 603 around the weakening portion 609. The handle bar is connected to the first mounting device 610 by screws or other fixation means through holes 611a, 611b. On the opposite side of first mounting device 610, there are also corresponding hoes 611c, 611d.

The smart handle apparatus 200 also has a second mounting device 612 which has holes 611e, 611f (not visible in FIG. 6) for fixing handle bar 603 to the second mounting device 612. Furthermore, the second mounting device 612 has a step 613a, 613b which is used for indicating a force strength and a force direction of a force applied to the handle bar.

The smart handle apparatus 200 is designed to sense a user request applied to the handle bar by the hand of a user in order to unlock a corresponding axis for a free movement. The smart handle apparatus may be adapted to lock and/or unlock a plurality of relevant joints driven by force applied to the handle bar with a single hand. Thus, the user may not need to think about which joint has to be locked and/or unlocked in order to perform a desired movement. The user is required to press the safety switch 607 before applying the force to maneuver translational axis or the plurality of axes. In order to maneuver rotational axis or the plurality of rotational axes, one of the control switches 606a, 606b is also required to be pressed along with the safety switch 607 before applying the force. The control switches 606a, 606b may either be triggered once a user touches the control switch 606a, 606b or has to be pressed during the time the smart handle apparatus is used in order to switch between the movement profile and to select a group of possible movements.

In order to sense the user request for each axis, the smart handle apparatus 200 in FIG. 6 uses optical devices or optical sensors. As an alternative, also force sensitive resistor (FSR) sensors can be used.

In the following, the function of a smart handle using optical devices is described. The description, however, can also be applied to smart handle apparatuses using an optical sensor, a force sensitive resistor, a strain gauge sensor, a capacitive sensor and/or a potentiometer.

For describing the functionality in combination with the safety switch 607 and control switches 606a, 606b and the force direction, reference is made to table 2.

TABLE 2

| Safety switch 607 | Any one Control switch 606a, 606b | Orbital/Propeller group of movements (A4, A5) | Wigwag/Horizontal/Height group of movement (A1, A2, A3) |
|---|---|---|---|
| OFF | No operation | | |
| ON | OFF | Allows individual axis or all axes movement based on force input in the respective direction. | No operation |
| ON | ON | No operation | Allows individual axis or all axes movement based on force input in the respective direction. |

A horizontal movement may comprise a carriage movement and/or a horizontal movement of an arm. If the safety switch 607 is not operated, exiting force to the handle bar 603 will have no effect. This function may prevent unintentional operation of the handle.

Pressing the safety switch 607 activates the smart handle apparatus 200. If any of the control switches 606a, 606b is not pressed, released or not operated, the first movement profile is selected and a first group of movements is activated. In the example of Table 2, the first group of movements includes the wig-wag rotational movement and the horizontal and height translational movements.

With the control switch 606a, 606b being pressed or switched on, the second group of movements can be controlled. In the example of Table 2, the second group includes the orbital and propeller rotational movements.

Thus, if the control switch 606a, 606b is switched on, individual axis or all axes movement based on force input in the respective direction which is used for orbital or propeller movement is enabled. Orbital and propeller movement do not intersect with each other and therefore a command provided via the handle 200 can be differentiated. In other words, moving a handle along the longitudinal axis 614 triggers the propeller movement profile, provided the smart handle bar is oriented in a horizontal position, where the longitudinal axis 614 is substantially parallel to the floor. If, however, the handle bar is in the position where the longitudinal axis 614 is parallel to the floor and the handle bar is moved into the z-direction, as indicated by Cartesian coordinate system 615, the C-arm would be caused to make an orbital movement.

Whether the handle 200 is in a horizontal or vertical orientation compared to the floor and/or to the direction of the G-force is sensed by an orientational sensor 602, 802a inside the handle bar 603. If the handle starts in a vertical position substantially parallel to the floor, the intuitive movement of a user to initiate the propeller movement is also to move the handle bar in the longitudinal direction 614, which is in the direction of the x-axis or substantially parallel to the floor. In any orientation, the orbital movement can be initiated by moving the handle bar with the handle 200 into the corresponding direction. A force direction determining device 708a, 708b, 708c (not shown in FIG. 6) is adapted to determine the force direction with regard to the handle coordinate system. The handle coordinate system may be a Cartesian coordinate system that is moved together with a movement of the handle 200. The force direction determining device is adapted to determine the direction of a force applied to the handle bar 603 in components of a three dimensional space, in particular with regard to the handle coordinate system. Furthermore, the orientation determining device 602, 802a is adapted to determine the orientation of the handle bar 603. This orientation determining device 602, 802a may further be adapted to determine the orientation of the handle bars' coordinate system.

The orientation of the handle bar and in particular the orientation of the coordinate system of the handle bar may be determined with regard to an earth coordinate system which does not move when the handle 200 is moving. The orientation of the coordinate system of the handle bar may be determined by detecting a gravity vector with the orientation determining device. The orientation determining device may comprise an accelerometer for determining the coordinates of the handle with regard to the earth coordinates. In other words, both devices may be used for determining a control signal. The force direction determining device is used to determine the force direction with regard to coordinates of the handle, detected through three force sensors, and an accelerometer is used for finding out the orientation of the coordinates of the handle with regards to earth coordinates by determining a gravity vector.

If, however, the C-arm is intended to move in a wig-wag direction, in the height or to execute carriage or horizontal movement, in addition to the safety switch 607, also the control switch 606a or 606b has to be switch on. Thus, if any of the control switches 606a, 606b is pressed or operated, the second movement profile is selected and a second group of movements is activated.

The control switches 606a, 606b are arranged parallel on the handle bar 603 or on two sides of the handle bar 603. If the control button 606a, 606b is switched on and the handle is moved, a movement along an individual axis or all axes based on the force of the input is possible. The amount of force applied into a respective direction may determine the velocity of the movement into this direction or determine whether a movement is made or not by comparing the amount of force to a threshold. The orbital and propeller movement is switched off and a movement in the respective direction, e.g. movement of the carriage, height or wigwag, is possible. In addition the orientation of the handle may be considered in order to determine the intention of the user with regard to the movement. For example, if the handle is in a horizontal position with regard to the floor and is moved along the x-axis and along the longitudinal axis 614 of the handle bar 603, a wig-wag movement is initiated. If the handle 200 is in a horizontal position with regard to the floor and is moved into the z-direction, a height adaption will be conducted, i.e. an up or down movement. And if the handle is in a horizontal position with regard to the floor and is pulled or pushed back and forth in the y-direction, the horizontal movement of the C-arm is the result. If the handle is in a vertical position with regard to the floor and is moved along the z-axis and perpendicular to the longitudinal axis 614 of the handle bar 603, a wig-wag movement is initiated. If the handle 200 is in a vertical position with regard to the floor and is moved into the x-direction, i.e. in the direction of the longitudinal axis 614, a height adaption will be conducted i.e. an up or down movement. And if the handle is in a vertical position with regard to the floor and is pulled or pushed back and forth in the y-direction, the horizontal movement of the C-arm is the result.

If an omni wheel may be used at the carriage 103a, in addition to the wig-wag movement the handle can also control a parallel movement to the floor.

Figure 7:
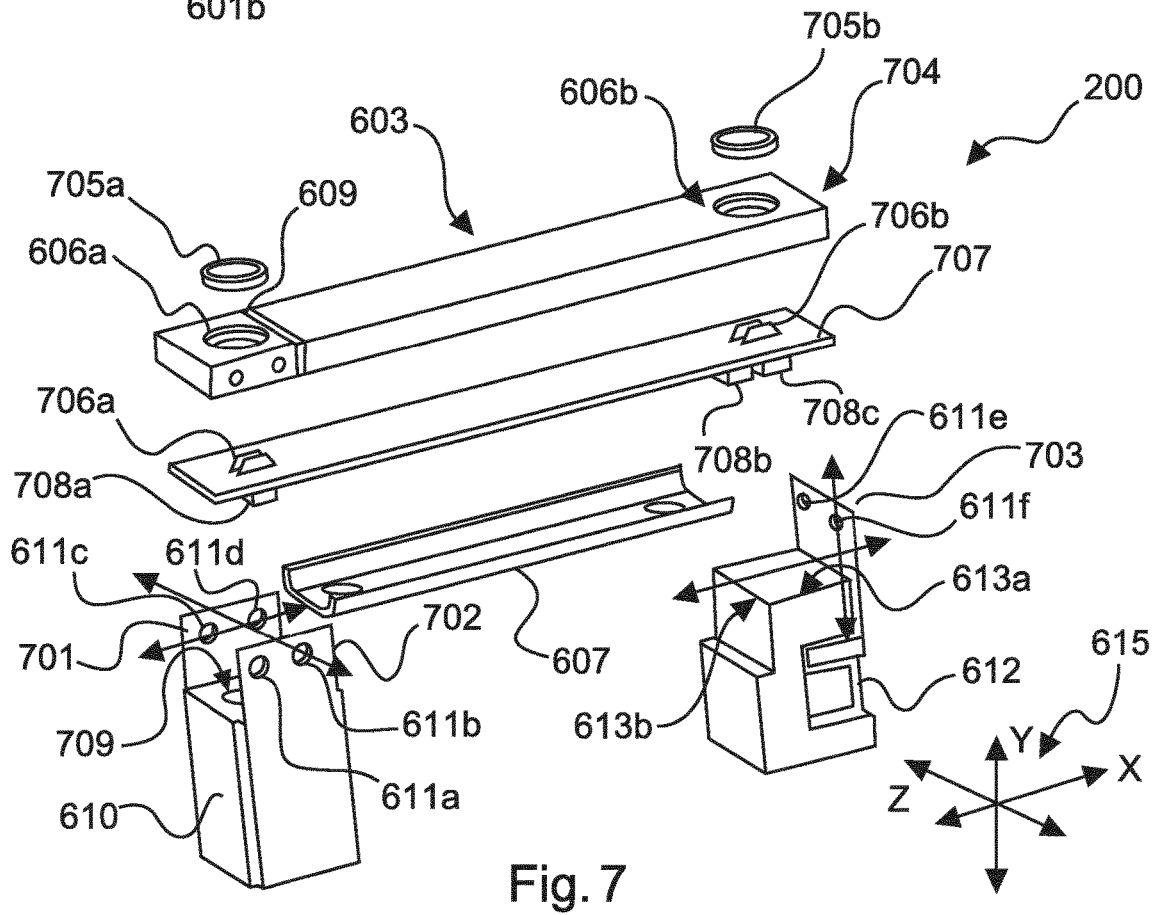
FIG. 7 shows an exploded view of the smart handle apparatus according to an exemplary embodiment of the present invention.

FIG. 7 shows an exploded view of the smart handle apparatus 200 according to an exemplary embodiment of the present invention. The first mounting device 610 has the two parallel flanges 701, 702 with the holes 611a, 611b, 611c, 611d. The parallel flanges 701, 702 are arranged on opposite sides of the first mounting device 610, parallel to a longitudinal axis of the handle bar 603 and are used to mount the smaller part in the longitudinal direction of the handle bar 603 compared to the weakening 609 onto the first mounting device 610. The second mounting device 612 has a flange 703 which is arranged perpendicular to a longitudinal axis of the handle bar 603 and has the holes 611e, 611f for mounting the handle bar 603 in a longitudinal direction on the small surface 704. As shown in FIG. 7, the buttons 606a, 606b comprise a silicon switch cover 705a, 705b in order to protect the switching devices 706b, 706a which are mounted on a bottom panel 707. Safety switch 607 is also mounted on the bottom panel 707 such that it can be moved parallel to the first mounting device 610 and the second mounting device 612.

FIG. 7 also shows an optical sensor 708a arranged in the direction of the first mounting device 610. This optical sensor is mounted on the bottom panel 707 in a position so that an optical beam generated by the optical sensor 708a can propagate into hole 709 of the first mounting device 610. On the opposite side at the second mounting device 612, optical sensor 708b is mounted on the bottom panel 707 in such a way, that the beam generated by optical sensors 708 is directed to the step 613b of the second mounting device. The optical sensor 708c is mounted on the bottom panel 707 in a position such that the beam propagates to the plane 613a of the second mounting device 612 where it is reflected.

Figure 8:
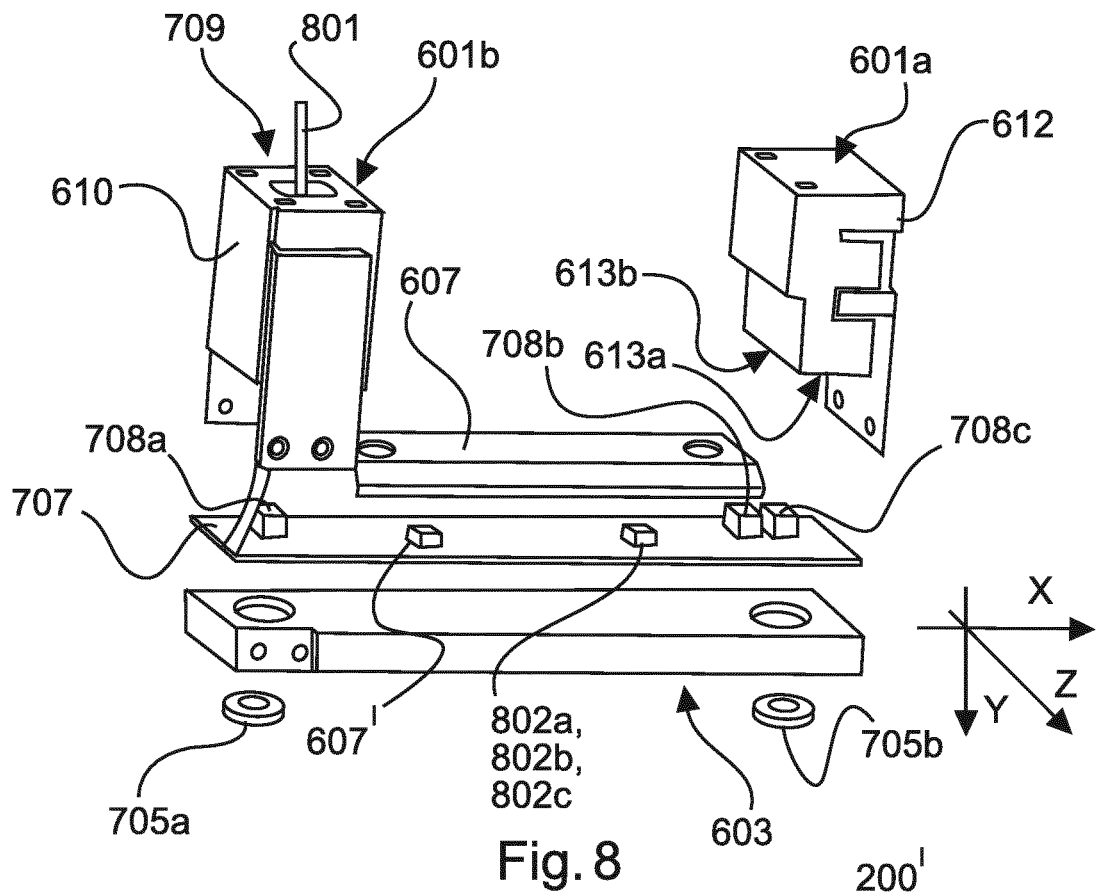
FIG. 8 shows a bottom view of the smart handle apparatus according to an exemplary embodiment of the present invention.

FIG. 8 shows a bottom view of the smart handle apparatus 200 according to an exemplary embodiment of the present invention. FIG. 8 shows the bottom view of hole 709 in the first mounting device 610. Optical sensor 708a sends an optical beam 801 through hole 709. If the handle bar 603 is moved into the z-direction, a parallelogram formed by flanges 701, 702 and holes 611a, 611b, 611c, 611d is moved or twisted so that the strength of a beam 801 reflected to the optical sensors 708a is varied or modulated according to the force applied in the z-direction, i.e. the direction perpendicular to a longitudinal axis 614 of the handle bar 603. Thus, the force into the z-direction can be measured with optical sensor 708a.

The beam generated by the optical sensor 708b is directed to the step 613b of the second mounting device 612 formed by the edge 613b of the second mounting device 612 at plane 613a. If the handle bar 603 is moved into the longitudinal direction or along the x-axis, the intensity of a reflected signal from this step 613b to optical sensor 708b is varied and optical sensor 708b provides the direction and strength of the force along the x-axis.

The optical sensor 708c generates an optical beam which is directed to the surface 613a of a plane of the second mounting device 612. This radiation is reflected to the optical sensor 708c and the intensity of that reflected beam is the measure for the distance between the optical sensor 708c and plane 613a. Moving the handle in the y-direction changes the distance between surface 613a and optical sensor 708c and thus a force in the y-direction and the strength of the force in the y-direction can be detected by the optical sensor 708c. Since handle bar 603 has a weakening portion 609 close to the first mounting device 610 the handle bar 603 forms a leaf spring construction that allows the handle bar 603 to be moved in direction parallel to flange 703. The leaf spring construction provides the compliance required for the movement.

On the bottom panel 707, the electronic board 707 or the PCB (Printed Circuit Board) assembly 707, other functional elements are mounted as well. For instance, on the bottom plane 707 or PCB 707, also the accelerometer 602, 802a or G-sensor 602, 802a and a communication device 802b as well as a mapping device 802c are mounted. The communication device 802b comprises a serial communication interface for a serial communication of the PCB 707 with the main controller of a controlling device for the handle apparatus. Via this serial interface signals between the PCB 707 and a controlling device may be exchanged. The mapping device 802c may be realized as a processor that runs an algorithm to interpret the direction and force and provides a signal indicating the intended motion. The signal may be generated by mapping signals received from sensors to control signals of the relevant actors by using a motion profile. The motion profile may help to identify the group of possible movements dependent on the switching state of button devices 606a, 606b.

As can also be seen in FIG. 8, the safety switch 607 is in contact with a safety switch detecting device 607' which is operated when the handle bar 603 is pressed. The safety switch 607 therefore is handled with a natural gripping action or with a natural grabbing action. Connectors and cables which are used to provide the signals of the various sensors 708a, 708b, 708c, 802a, 802b, 802c, 607' are not shown in FIG. 8.

Figure 9:
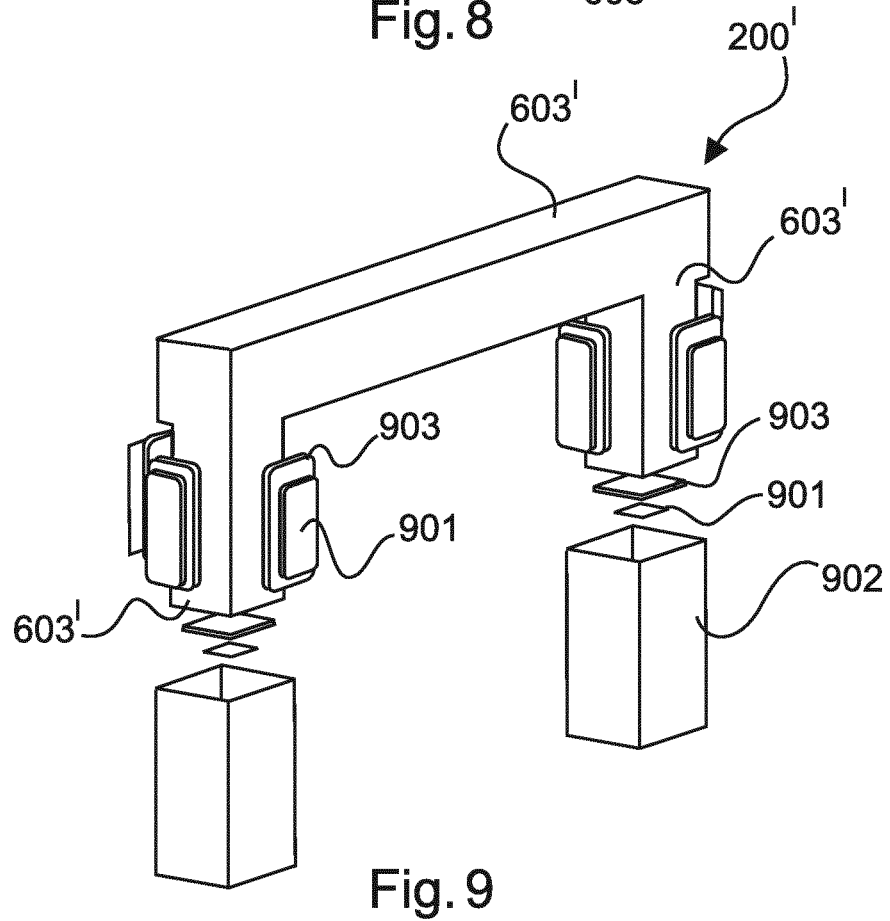
FIG. 9 shows an alternative smart handle apparatus according to an exemplary embodiment of the present invention.

FIG. 9 shows an alternative smart handle apparatus 200' according to an exemplary embodiment of the present invention. The handle bar 603' in FIG. 9 is made as a U-shaped stiff handle bar. In order to make the handlebar rigid it is made in one piece or monolithically. The handle bar 603' is a homogeneous body which is relatively stiff. On the handle bar 200', various FSR elements 901 and dampers 903 are mounted. In this design, force sensitive resistors (FSR) are used to calculate the direction and amount of force applied on the handle from all the directions. A resistance of the force sensitive resistor increases if the force increases applied to the resistor and decreases if the force decreases. All the FSRs 901 are mounted on either the wall of the leg of the handle with a damper assembly and/or on the inner wall of the outer box 902 of the leg. In that case when FSR is mounted on the inner wall of covering box 902, the damper will only be mounted on the leg of the handle and the handle will go or move inside the box. The two legs are used for mounting the handle 603'. The two legs of the handle 603' comprise a housing 902 which provides a fixed surface. The FSRs 901 and dampers 903 are arranged between the handle 603' surface and the housing 902 surface. In this way the FSR is compressed inside the housing 902 if the handle moves inside the housing 902. This movement which is translated into a compression can be measured by the change of resistance of the respective FSR. The damper in between the FSR and the housing ensures uniform contact and distribution of the force over the sensor. The damper will uniformly distribute the force on the FSR and will also help to retrieve back the position of the handle on releasing of the force. The outer box 902 will be fixed with the C-arm and the handle 603' will get inside the box. In association with all this, there will be a safety switch and two optional switches at the top of the handle to control the various locking mechanisms of the C-arm in correspondence with the various movements of the C-arm. With this design, an efficient control of the speed of the movements of the C-arm in various directions may be possible in a case where the axes or joints are motor-driven and controlled by the smart handle.

Figure 10:
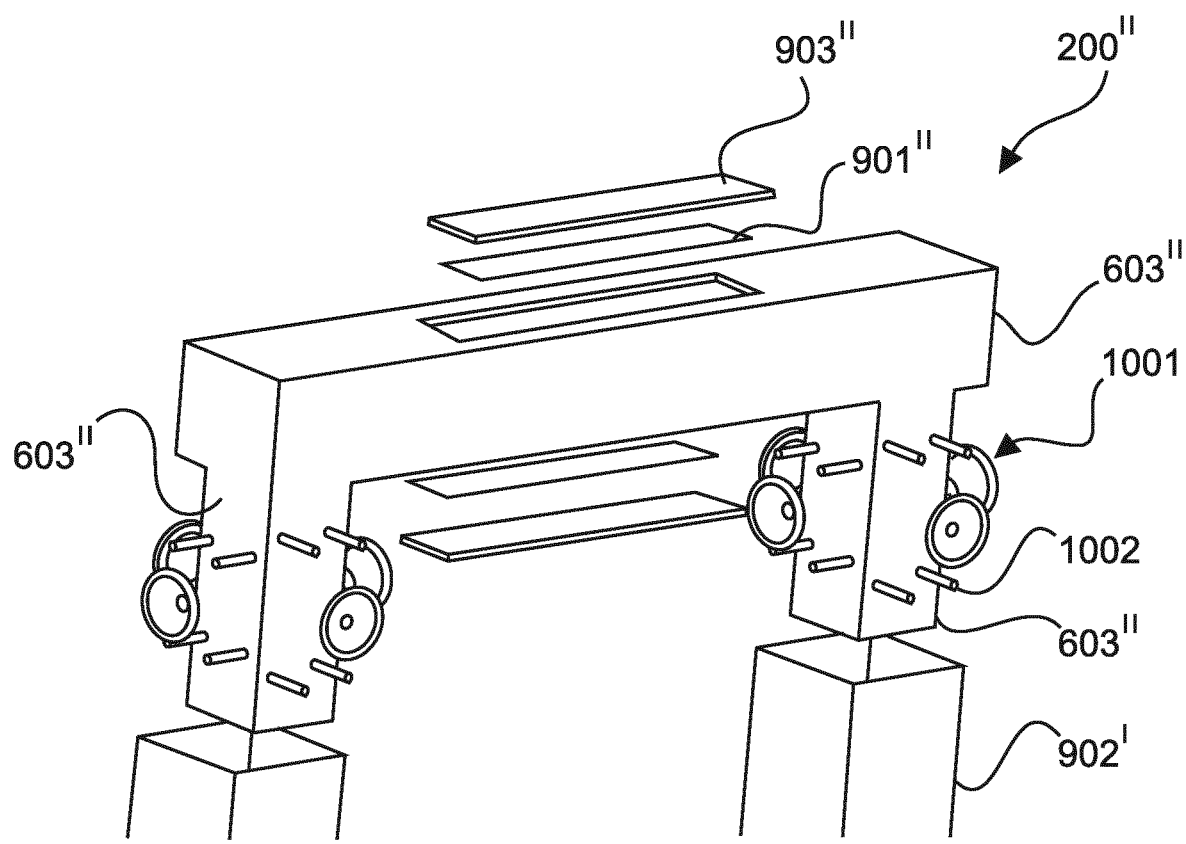
FIG. 10 shows a further alternative smart handle apparatus according to an exemplary embodiment of the present invention.

FIG. 10 shows an alternative smart handle apparatus 200" according to an exemplary embodiment of the present invention. A design according to FIG. 10 comprises a plurality of combination of a low profile tact switches 1001 or low profile tactile switches 1001. Tact switches 1001 are installed in the inner wall of the outer box 902' on all sides of the monolithic handle bar 603". Whenever the handle 200" is forced to move in any direction, the corresponding switch 1001 will be pressed and generates a signal. Springs 1002 are used to damp the movement of the handle 603' within the outer box 902'. The FSR 903" and damper 901" are used to sense and calculate the amount of vertical force applied in the handle. The vertical force is a force in the direction parallel to the y axis or parallel to the legs of handle 200". The FSRs 903", 901" mounted on both sides of the handle can also act as the safety switch to enable the smart handle bar 200". The FSR 903" can also be calibrated to sense the amount of force applied in the handle 603" ranging from just simply touching the handle up to a large force applied to it.

Figure 11:
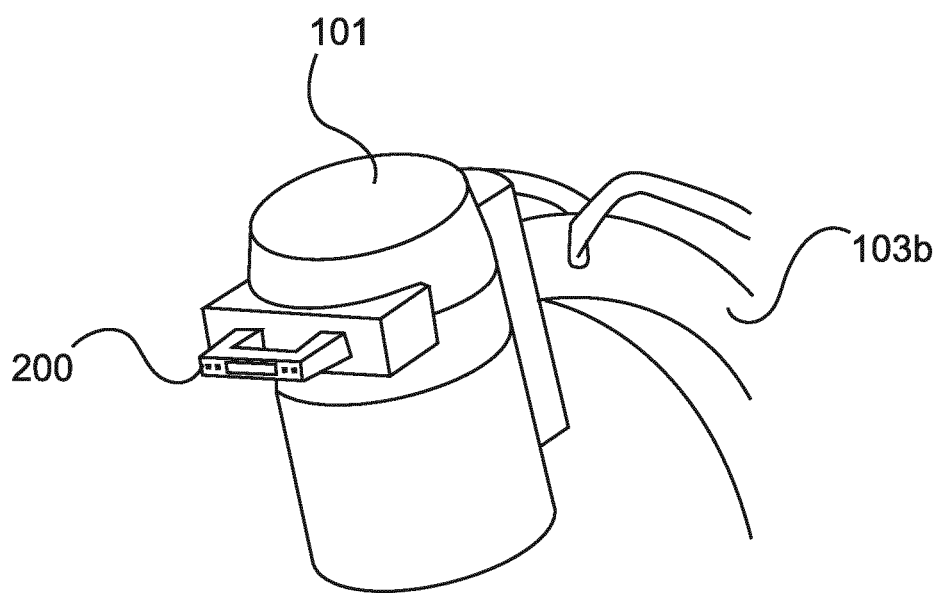
FIG. 11 shows an extract of the C-arm with the smart handle according to an exemplary embodiment of the present invention.

FIG. 11 shows an extract of the C-arm 103b with the smart handle according to an exemplary embodiment of the present invention. The smart handle 200 is attached to the X-ray source 101 of the C-arm of the mobile surgery system. In particular, the smart handle 200 is mounted on the C-arm 101 at front of the image detector side. An operator who is using the smart handle apparatus 200 with his hand can maneuver at the same time more than one axis by applying force in respective direction to the smart handle. For instance, if the user applies a force in a direction of 45 degrees to the orbital and rotational direction and this force exceeds the threshold set for both directions then both axes can be unlocked to allow simultaneous motion. The axes will be locked again when the forces fall below the threshold. Even if in FIG. 11 an embodiment is shown where the smart handle is mounted on the X-ray detector side, the inventive smart handle apparatus 200, 200", 200' can be mounted anywhere on the C-arm to maneuver the different axes. A corresponding orientation sensor of the handle device has to be calibrated to the corresponding mounting position in order to allow the right movement of the C-arm.

If the handle is mounted on a different position of the C-arm the orientation of the handle has to be calibrated in order to set the default or zero orientation. The smart handle device 200 is visible on the system as a user interface 200. The smart handle 200 can replace physical lock and unlock handles which are mounted at every joint and which need to be operated by a technician. If the smart handle is used, then manual lock and/or unlock handles are not needed. Electromagnetic brakes located inside the system will lock and/or unlock the joints wherein the electromagnetic brakes are controlled by the smart handle. The smart handle can be used to maneuver each axis intuitively. The smart handle also allows for individually releasing the joint which is involved in the desired movement and prevents a situation, where all joints are locked or unlocked independently on the force and direction of the force of the handle. With the smart handle 200, 200', 200'' automatic locking and unlocking of a mobile C-arms' rotational and translational movement is possible and can manually and intuitively be controlled. It may help optimizing a workflow and may prevent mistakes during the surgery procedure.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mobile surgery imaging system including a C arm and a smart handle apparatus configured to control movements of the imaging system, the smart handle apparatus comprising:
 a handle bar for operating the smart handle apparatus;
 a force determining device;
 a button device;
 wherein the force determining device is adapted to determine the direction of a force applied to the handle bar in components of a three dimensional space;
 wherein the button device is adapted to select a first or second movement profile corresponding to respective groups of movements wherein, within a group, each movement is linkable to a corresponding direction component of the three dimensional space determined by the force determining device;
 wherein the smart handle apparatus is adapted to provide a control signal for moving the mobile surgery imaging system, the control signal comprising information about a selected movement profile and a determined direction of the force applied to the handle bar.

2. The mobile surgery system according to claim 1, the smart handle apparatus further comprising:
 an orientation determining device;
 wherein the orientation determining device is adapted to determine the orientation of the handle bar;
 wherein the smart handle apparatus is further adapted to provide information about the determined orientation of the handle bar in the control signal.

3. The mobile surgery system according to claim 2, wherein the orientation determining device of the smart handle apparatus comprises an accelerator sensor and/or a G-force sensor.

4. The mobile surgery system according to claim 2, wherein the smart handle apparatus is mounted on an X-ray source or an X-ray detector of the C-arm.

5. The mobile surgery system according to claim 1, wherein the force determining device of the smart handle apparatus is further adapted to determine the strength of each component of the force in each direction of the three dimensional space;
 wherein the smart handle apparatus is further adapted to provide information about the determined strength of each component of the force in each direction of the three dimensional space in the control signal.

6. The mobile surgery system according to claim 5, the smart handle apparatus further comprising:
 a mapping device;
 wherein the mapping device is adapted to map the information of the control signal to a predefined movement of the set movement profile.

7. The mobile surgery system according to claim 6, wherein the movement profile comprises a group of movements. each group of movements comprising a selection of movements of:
 a height positioning movement;
 a horizontal movement;
 a propeller movement;
 a wig-wag movement; and
 an orbital movement.

8. The mobile surgery system according to claim 7, the smart handle apparatus further comprising a second button device adapted to set a movement profile in form of groups of movements;
 wherein the second button device is arranged in a predefined distance from the button device.

9. The mobile surgery system according to claim 8, wherein the force determining device of the smart handle apparatus comprises at least one of an optical sensor, a force sensitive resistor, a strain gauge sensor, a capacitive sensor and/or a potentiometer.

10. The mobile surgery system according to claim 1, wherein the force determining device of the smart handle apparatus comprises a threshold;
 wherein the force determining device is adapted to prevent delivering of signals below the threshold.

11. The mobile surgery system according to claim 1, the smart handle apparatus further comprising a safety switch, wherein the safety switch is adapted to prevent an unintentional operation.

12. A non-transitory computer-readable storage medium having stored therein a computer program containing instructions for controlling a smart handle apparatus according to claim 1, in accordance with a method of controlling movements of a mobile surgery imaging system comprising the steps of:
- determining the direction of a force applied to a handle bar of the smart handle apparatus in components of a three dimensional space;
- selecting a first or second movement profile corresponding to respective groups of movements by a button device;
- wherein each movement within a group is linkable to a corresponding direction component of the three dimensional space determined by the force determining device:
- providing a control signal comprising information about the selected movement profile and the direction of the force applied to the smart handle apparatus.

13. A method for controlling a mobile surgery imaging system comprising:
- determining the direction of a force applied to a handle bar of a smart handle apparatus in components of a three dimensional space;
- selecting a first or second movement profile corresponding to respective groups of movements by a button device;
- wherein each movement within a group is linkable to a corresponding direction component of the three dimensional space determined by the force determining device;
- providing a control signal comprising information about the selected movement profile and the direction of the force applied to the smart handle apparatus.

14. The method of claim 13, further comprising
controlling movements of a mobile surgery imaging system in accordance with the control signal.

* * * * *